US009222894B2

(12) United States Patent  
Park et al.

(10) Patent No.: US 9,222,894 B2
(45) Date of Patent: Dec. 29, 2015

(54) DETECTION DEVICE FOR DETECTING STATE OF TONER IMAGE, IMAGE FORMING APPARATUS EMPLOYING THE SAME, AND METHOD OF REMOVING FOREIGN SUBSTANCE FROM THE DETECTION DEVICE

(71) Applicant: SAMSUNG ELECTRONICS CO., LTD., Suwon (KR)

(72) Inventors: Eun-seok Park, Goyang (KR); Jong-cheol Oh, Suwon (KR)

(73) Assignee: SAMSUNG ELECTRONICS CO., LTD., Suwon-Si (KR)

(*) Notice: Subject to any disclaimer, the term of this patent is extended or adjusted under 35 U.S.C. 154(b) by 0 days.

(21) Appl. No.: 13/953,333

(22) Filed: Jul. 29, 2013

(65) Prior Publication Data

US 2014/0147152 A1 May 29, 2014

(30) Foreign Application Priority Data

Nov. 26, 2012 (KR) ................ 10-2012-0134872

(51) Int. Cl.
*G03G 21/00* (2006.01)
*G01N 21/94* (2006.01)
*B08B 6/00* (2006.01)
*G03G 15/00* (2006.01)
*G03G 15/08* (2006.01)

(52) U.S. Cl.
CPC ...... *G01N 21/94* (2013.01); *B08B 6/00* (2013.01); *G03G 15/0855* (2013.01); *G03G 15/5058* (2013.01)

(58) Field of Classification Search
USPC ................................... 399/34, 74, 30
See application file for complete search history.

(56) References Cited

U.S. PATENT DOCUMENTS

| 4,110,027 | A | * | 8/1978 | Sato et al. | 399/317 |
| 5,019,871 | A | * | 5/1991 | Takeda et al. | 399/66 |
| 7,845,757 | B2 | * | 12/2010 | Nishiyama | 347/23 |
| 2009/0016768 | A1 | * | 1/2009 | Seorl et al. | 399/107 |
| 2012/0301183 | A1 | * | 11/2012 | Seorl et al. | 399/114 |
| 2013/0243471 | A1 | * | 9/2013 | Ikeda et al. | 399/93 |

* cited by examiner

*Primary Examiner* — Clayton E Laballe
*Assistant Examiner* — Warren K Fenwick
(74) *Attorney, Agent, or Firm* — Staas & Halsey LLP

(57) ABSTRACT

A detection device detecting a state of a toner image, an image forming apparatus including a detection device and method of detection are provided. The detection device includes a detector having a light window where light passes through and detecting a state of a toner image formed on an image bearing member via the light window, and a cleaner removing a pollutant attached to a surface of the light window. The cleaner includes an adsorption unit formed of a conductive material and reciprocating while being in contact with the surface of the light window and a voltage applying unit applying a voltage for adsorbing the pollutant to the adsorption unit.

33 Claims, 14 Drawing Sheets

DETECTION DEVICE FOR DETECTING STATE OF TONER IMAGE, IMAGE FORMING APPARATUS EMPLOYING THE SAME, AND METHOD OF REMOVING FOREIGN SUBSTANCE FROM THE DETECTION DEVICE

CROSS-REFERENCE TO RELATED APPLICATIONS

This application is related to, and claims priority to, Korean Patent Application No. 10-2012-134872, filed on Nov. 26, 2012, in the Korean Intellectual Property Office, the disclosure of which is incorporated herein by reference.

BACKGROUND

1. Field

Embodiments of the present invention relate to a detection device for detecting a state of a toner image, an image forming apparatus employing the detection device, and a method of removing foreign substances from the detection device, and more particularly, to a detection device capable of reducing a detection error by preventing contamination of the detection device, an image forming apparatus employing the detection device, and a method of removing foreign substances from the detection device.

2. Description of the Related Art

An image forming apparatus forms an electrostatic latent image on a photosensitive body by an exposure operation, forms a toner image on the photosensitive body by supplying toner, transfers the toner image formed on the photosensitive body to a printing medium, and fixes the transferred toner image to the printing medium by using heat and pressure, thereby performing printing.

However, in a case of the toner image formed on the photosensitive body, a state of the toner image such as concentration and an aligned state of the toner image may deviate from predetermined standards due to environmental effects such as temperature and humidity while performing a transfer operation. To address such problems, a state of the toner image may be detected, a concentration may be adjusted according to a value obtained by detection, or the aligned state may be adjusted.

However, since a detection device detecting a state of a toner image may be disposed adjacent to an image bearing member with the toner image formed such as a photosensitive body to detect the toner image, the detection device may be contaminated contaminate by foreign substances such as scattered toner while forming the toner image. Such contamination of the detection device generates a detection error, which makes an adjustment operation according thereto indefinite.

SUMMARY

Additional aspects and/or advantages will be set forth in part in the description which follows and, in part, will be apparent from the description, or may be learned by practice of the invention.

An exemplary embodiment of the present invention provides a detection device of an image forming apparatus, the detection device capable of reducing detection errors generated by a foreign substance attached to the detection device.

An exemplary embodiment of the present invention provides an image forming apparatus including a detection device and a method of removing a foreign substance from the detection device.

According to an aspect of the present invention, a detection device is provided. The detection device includes a detector having a light window where light passes through and detecting a state of a toner image formed on an image bearing member via the light window, and a cleaner removing a pollutant attached to a surface of the light window. The cleaner includes an adsorption unit formed of a conductive material and reciprocating while being in contact with the surface of the light window and a voltage applying unit applying a first voltage for adsorbing the pollutant to the adsorption unit.

The adsorption unit may be capable of being transferred to a first location for being in contact with the light window and a second location for releasing a contact with the light window.

The voltage applying unit may apply the first voltage for adsorbing the pollutant to the adsorption unit when the adsorption unit is located in the first location.

The first voltage may be a voltage having polarity opposite to the pollutant.

The polarity of the first voltage may be periodically converted.

The cleaner may include a pollutant collecting unit collecting the pollutant.

The pollutant collecting unit may include a contact projection projected crossing a transfer path of the adsorption unit and being in contact with the adsorption unit.

The voltage applying unit may apply a second voltage for separating the pollutant from the adsorption unit to the adsorption unit when the adsorption unit is located in the second location.

The second voltage may be one of a voltage having the same polarity as the pollutant and a ground voltage.

The voltage applying unit may apply a third voltage for collecting the pollutant into the pollutant collecting unit to the pollutant collecting unit when the adsorption unit is located in the second location.

The third voltage may be a voltage having polarity opposite to the pollutant.

The voltage applying unit may apply a fourth voltage for preventing the pollutant being attached to the light window to the adsorption unit.

The fourth voltage may be one of a voltage having the same polarity as the pollutant and a ground voltage.

The detection device may include a housing containing the detector, the housing with an opening between the light window and the image bearing member to allow light to pass through, and a shutter opening and closing the opening.

The adsorption unit may be installed on a surface of the shutter facing the detector, and the adsorption unit may remove the pollutant attached to the light window by a transfer of the shutter.

According to an aspect of the present general inventive concept, there is provided an image forming apparatus including the detection device.

The apparatus may include a housing containing the detector, the housing with an opening between the light window and the image bearing member to allow light to pass through, and a shutter opening and closing the opening.

The adsorption unit may be installed on a surface of the shutter facing the detector, and the adsorption unit may remove the pollutant attached to the light window by a transfer of the shutter.

According to an aspect of the present invention, there is provided a method of removing pollutant, performed by a detection device detecting a state of a toner image formed on an image bearing member. The method includes applying, to adsorb pollutant attached to a light window of a detector, a first voltage for adsorbing the pollutant to an adsorption unit reciprocating while being in contact with the light window, and allowing the pollutant to be adsorbed onto the adsorption unit by using electrical fundamental forces generated between the adsorption unit and the pollutant.

In the allowing the pollutant to be adsorbed onto the adsorption unit, the adsorption unit may be located in a location for being in contact with the light window.

The first voltage may be a voltage having polarity opposite to the pollutant.

The polarity of the first voltage may be periodically converted.

The method may include after the allowing the pollutant to be adsorbed onto the adsorption unit, separating the pollutant adsorbed onto the adsorption unit.

In the separating the pollutant, the adsorption unit may be located in a location for releasing a contact with the light window.

In the separating the pollutant, the adsorption unit may be transferred while being in contact with a contact projection formed on a pollutant collecting unit.

In the separating the pollutant, a second voltage for separating the pollutant adsorbed onto the adsorption unit may be applied the adsorption unit.

The second voltage may be one of a voltage having the same polarity as the pollutant and a ground voltage.

In the separating the pollutant, a third voltage for collecting the pollutant into the pollutant collecting unit may be applied to the pollutant collecting unit.

The third voltage may be a voltage having polarity opposite to the pollutant.

After the separating the pollutant, a fourth voltage for preventing the pollutant being attached to the light window may be applied to the adsorption unit.

The method may include determining an exposure of the detector via a transfer of a shutter arranged between the image bearing member and the detector.

The adsorption unit may be installed on a surface of the shutter facing the detector and removes the pollutant attached to the light window by using the transfer of the shutter.

The detection device, the image forming apparatus and the method of removing pollutant by using the detection device may improve efficiency of removing pollutant attached to the detection device by using mechanical friction and electrical fundamental forces to remove the pollutant. Also, detection errors are reduced and a state of a toner image is corrected without error according to a detected value, thereby improving quality of printed images.

BRIEF DESCRIPTION OF THE DRAWINGS

The above and other features and advantages of the present general inventive concept will become more apparent by describing in detail exemplary embodiments thereof with reference to the attached drawings in which.

DETAILED DESCRIPTION

Exemplary embodiments of the present invention are disclosed with reference to the accompanying drawings, in which exemplary embodiments of the present invention are illustrated.

Figure 1:
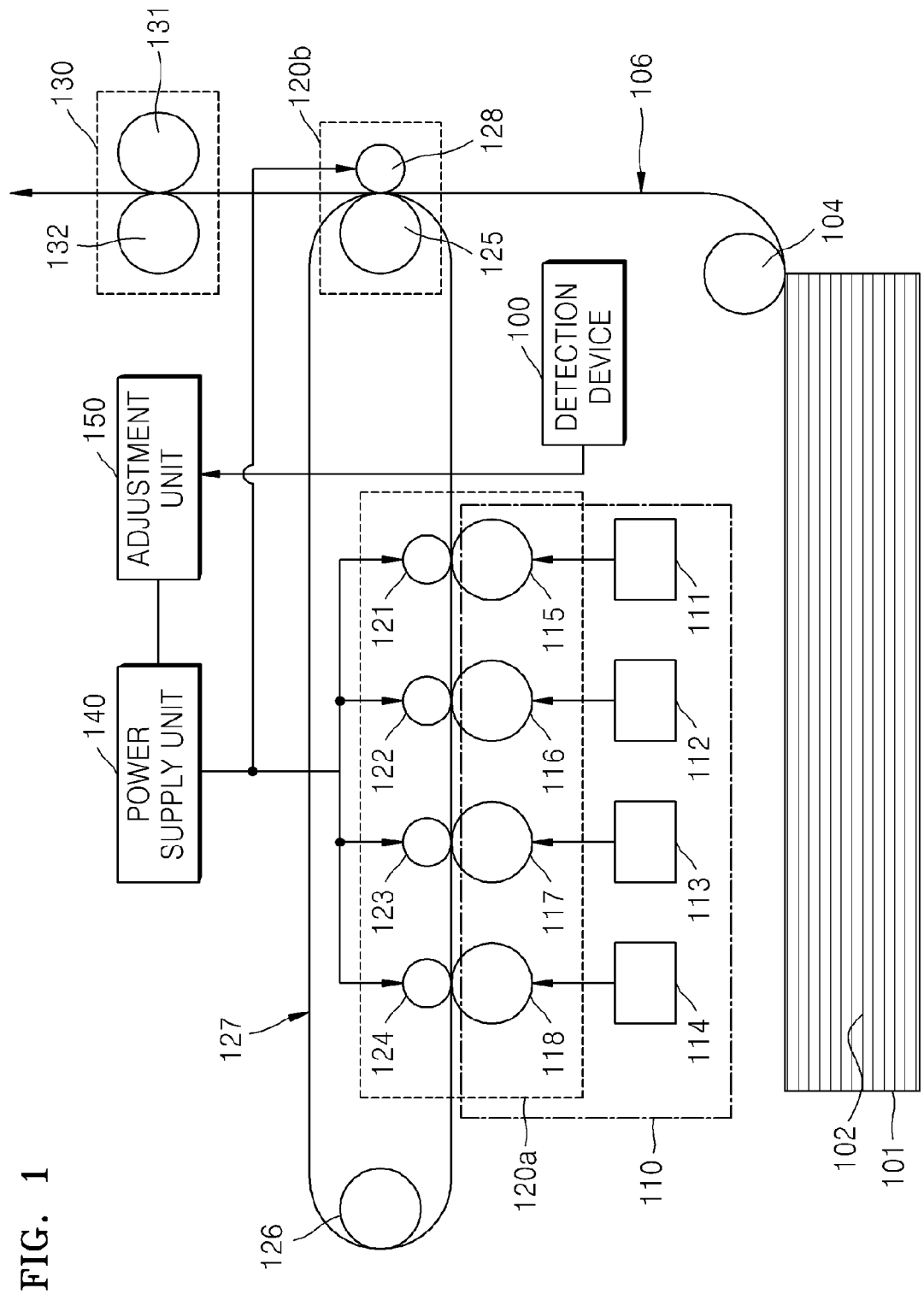
FIG. 1 illustrates an image forming apparatus according to an embodiment of the present invention.

FIG. 1 illustrates an image forming apparatus according to an exemplary embodiment of the present invention. The image forming apparatus may include a development unit 110, transfer units 120a and 120b, a fixing unit 130, a power supply unit 140, an adjustment unit 150, and a detection device 100. The transfer units 120a and 120b may include additional transfer units.

According to an exemplary embodiment of the image forming apparatus, when image data is received from the outside, the development unit 110 develops an image. Exposure units 111 to 114 inject light to photosensitive bodies 115 to 118, electrostatic latent images may be formed on the photosensitive bodies 115 to 118, respectively, electrified toner may be supplied thereto, and toner particles may be attached to surfaces of the photosensitive bodies 115 to 118, thereby forming toner images. To form the toner images, not illustrated in FIG. 1, the development unit 110 may include an electrification element in contact with the photosensitive bodies 115 to 118 to electrify the surfaces of the photosensitive bodies 115 to 118, a developing element supplying toner to the photosensitive bodies 115 to 118, and a cleaning element cleaning the surfaces of the photosensitive bodies 115 to 118. Although four exposure units 111 to 114 and the four photosensitive bodies 115 to 118 are illustrated in FIG. 1, an exemplary image forming apparatus forming a color image and including photosensitive bodies and exposure units for four colors such as cyan, magenta, yellow, and black, respectively, is not limited thereto.

The toner images formed on the photosensitive bodies 115 to 118 may be transferred from the first transfer unit 120a to an intermediate transfer belt 127. To the intermediate transfer belt 127 rotated by intermediate transfer rollers 125 and 126, images corresponding to respective colors of cyan, magenta, yellow, and black, respectively, may be sequentially transferred, thereby forming a color toner image. The toner images formed on the intermediate transfer belt 127 may be transferred from the second transfer unit 120b to a printing medium 102. Although FIG. 1 illustrates the toner images are transferred from the photosensitive bodies 115 to 118 to the intermediate transfer belt 127 and then transferred from the intermediate transfer belt 127 to the printing medium 102, which is an example of an indirect transfer method, it is possible to directly transfer images from the photosensitive bodies 115 to 118 to a printing medium. The photosensitive bodies 115 to 118 or the intermediate transfer belt 127, on which toner images are formed, may be designated as image bearing members.

The printing medium 102 with an image transferred may be transferred along a transfer path 106 for the printing medium 102 to the fixing unit 130 to be heated and pressurized by fixing rollers 131 and 132. Accordingly, the image may be fixed to the printing medium 102, thereby completing an image forming process. The printing medium 102 may be contained in a feeding unit 101.

A transfer process, in the image forming process, performed by the transfer units 120*a* and 120*b* is disclosed. The power supply unit 140 supplies transfer voltages to the first transfer unit 120*a* and the second transfer unit 120*b*. To transfer images formed on the photosensitive bodies 115 to 118 to the intermediate transfer belt 127, the power supply unit 140 applies first transfer voltages to first transfer rollers 121 to 124. The first transfer voltages have polarity opposite to that of the toner images on the surfaces of the photosensitive bodies 115 to 118. The toner images on the surfaces of the photosensitive bodies 115 to 118 may be transferred to the intermediate transfer belt 127 by an electrostatic force provided by the first transfer voltages. When a second transfer voltage is supplied to a second transfer roller 128 by the power supply unit 140, the toner images may be transferred from the intermediate transfer belt 127 to a surface of the printing medium 102 transferred along the transfer path 106 for the printing medium 102.

The concentration of the transferred toner image may be affected by a transfer voltage. Due to various environmental factors such as a temperature and humidity, a desired concentration may deviate from a concentration of an actually outputted image. Accordingly, to output an image with a desired concentration, a concentration adjustment may be performed. An exemplary method of performing a concentration adjustment by using the detection device 100 is disclosed.

The detection device 100 detects a state of the toner image formed on the intermediate transfer belt 127, for example, the concentration of the toner image. According to a result of comparing a concentration value of the toner image detected by the detection device 100 with a preset reference concentration value, the adjustment unit 150 controls the power supply unit 140 to control the transfer voltages supplied to the transfer units 120*a* and 120*b*.

While the detection device 100 is detecting the concentration of the toner image of the intermediate transfer belt 127 that is an image bearing member, a foreign substance such as scattered toner may stick to the surface of the detection device 100 and may contaminate the detection device 100. Such contamination of the detection device 100 may cause a detection error, thereby preventing accurate concentration adjustment. Accordingly, to perform an accurate concentration adjustment, it may be necessary to prevent the contamination of the detection device 100. A cleaner 20 (as illustrated in FIG. 2) for the detection device 100 may bean element for removing a pollutant attached to a detector 10 (see, for example, FIG. 2).

Figure 2:
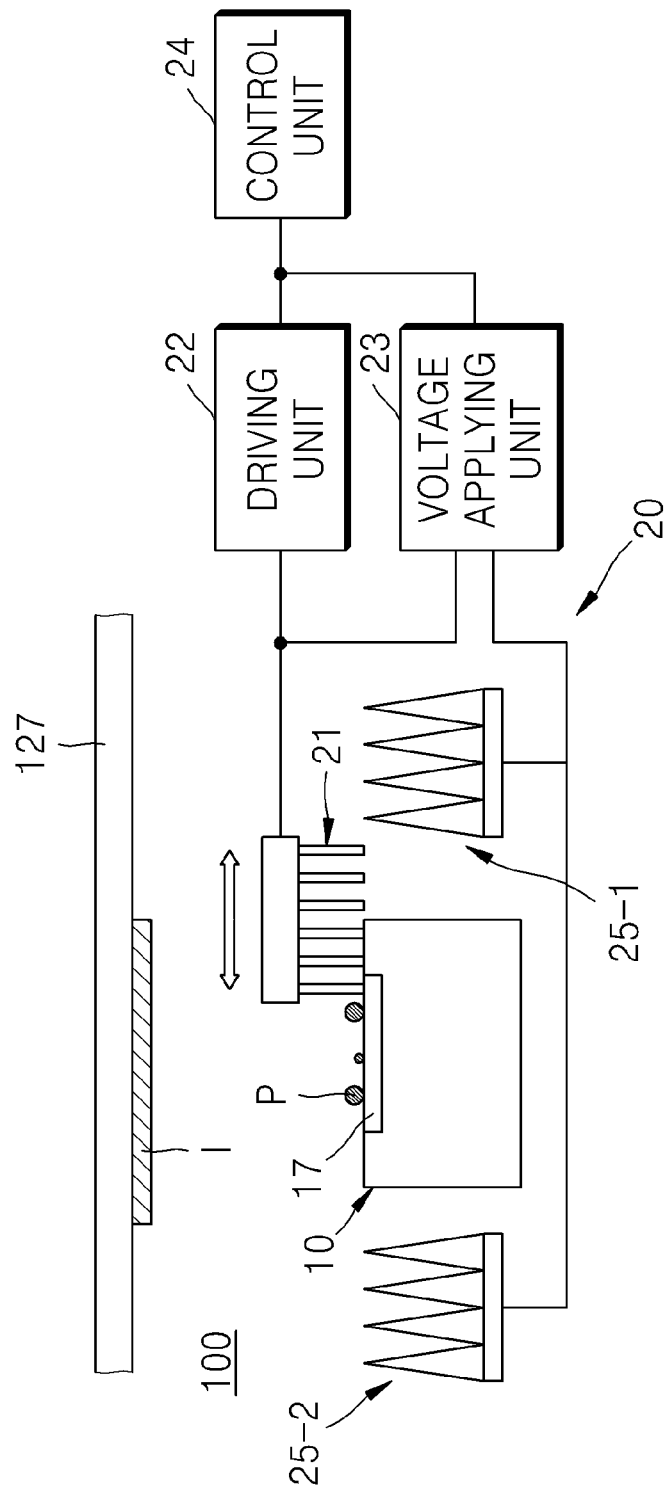
FIG. 2 illustrates a detection device included in an image forming apparatus according to an embodiment of the present invention.
Figure 3:
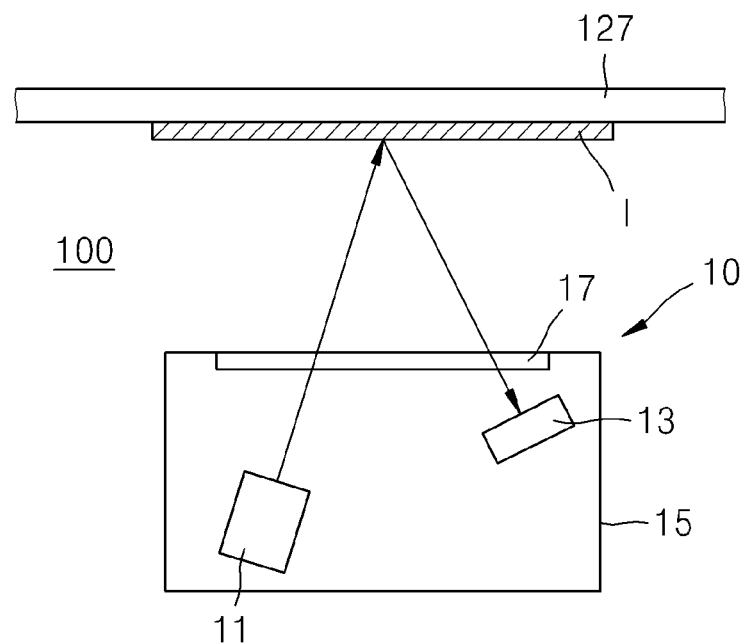
FIGS. 3 and 4 illustrate an exemplary detector included in a detection device.
Figure 4:
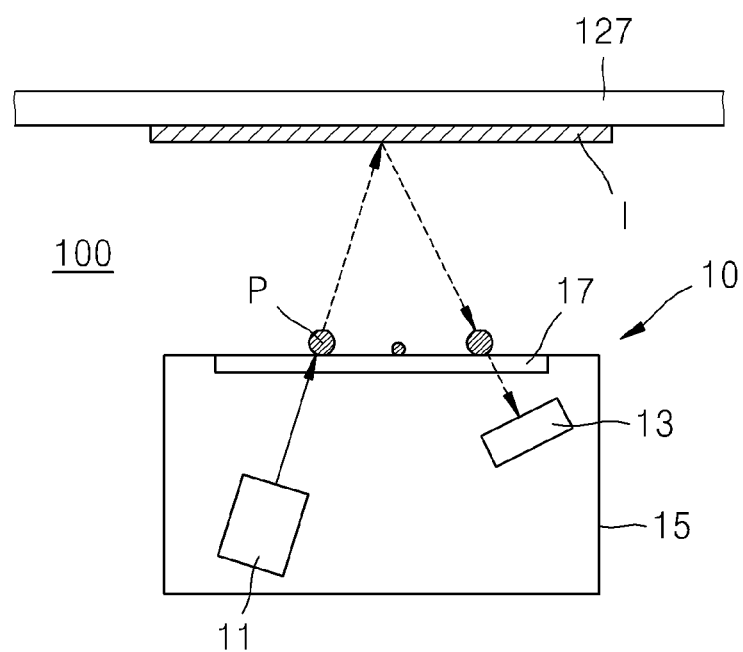

FIG. 2 illustrates an exemplary detection device 100 included in the image forming apparatus of FIG. 1 according to an embodiment of the present invention. FIGS. 3 and 4 illustrate a detector 10 that is an element of the detection device 100.

Referring to FIG. 2, the detection device 100 may include the detector 10 detecting a state of a toner image I such as a concentration thereof and the cleaner 20 removing the pollutant P attached to the detector 10.

The detector 10 detects the state of the toner image I such as concentration thereof. However, as described above, the detector 10 may be contaminated by the pollutant P while detecting the state of the toner image I. Referring to FIGS. 3 and 4, an exemplary occurrence of a detection error caused by the contaminated detection device 100 is disclosed.

Referring to FIG. 3, in a process of detecting the concentration of the toner image I on the intermediate transfer belt 127 performed by the detector 10, a light emitting unit 11 emits light to the toner image I formed on the intermediate transfer belt 127. As an example of the light emitting unit 11, a light emitting diode (LED) or a semiconductor laser diode may be used. A light receiving unit 13 receives reflected light that is the light emitted from the light emitting unit 11 to the toner image I and reflected therefrom and detects the concentration of the toner image I from a variance of a light strength of the reflected light. A casing 15 contains the light emitting unit 11 and the light receiving unit 13 and a light window 17 formed of a transmission (or transparent) material is located on a part of the casing 15. The light emitted from the light emitting unit 11 and the reflected light from the toner image I penetrate the light window 17. The light window 17 may prevent penetration of the pollutant P outside the casing 15 into the casing 15.

While the toner image I is being transferred onto the intermediate transfer belt 127, the pollutant P such as scattered toner float around the detector 10 and a part thereof is attached to a surface of the light window 17 as illustrated in FIG. 4. When the pollutant P are attached to the surface of the light window 17, the light emitted from the light emitting unit 11 or the reflected light from the toner image I are reflected from the pollutant P or refracts in such a way that the reflected light may not reach the light receiving unit 13 or a light strength of the reflected light reaching the light receiving unit 13 may not accurately reflect on the concentration of the toner image I.

Referring to FIG. 2, the cleaner 20 may reciprocate being in contact with the surface of the light window 17. While the cleaner 20 is reciprocating, mechanical friction may be applied onto the pollutant P in contact with the cleaner 20, thereby removing a part of the pollutant P attached to the light window 17. However, by only using such mechanical friction, the pollutant P attached to the light window 17 may not be completely removed. Pollutant P detached from the light window 17 may be scattered and attached to the light window 17. When the light window 17 is formed of a material to allow an occurrence of an electrostatic force due to the friction, such as a transparent polycarbonate, the pollutant P may be easily attached to the light window 17.

According to an exemplary embodiment, the cleaner 20 of the detection device 100 may be formed to remove the pollutant P attached to the light window 17 by applying electrical fundamental forces or repulsive forces in addition to the mechanical friction to the pollutant P attached to the light window 17. The cleaner 20 may include an adsorption unit 21, a driving unit 22 transferring the adsorption unit 21, a voltage applying unit 23 applying a voltage to the adsorption unit 21, and a control unit 24 controlling the driving unit 22 and the voltage applying unit 23.

The adsorption unit 21 may be in contact with the surface of the light window 17 and have a conductive material. For example, the material of the adsorption unit 21 may be conductive fibers. However, the material of the adsorption unit 21 is not limited thereto and may be various conductive materials. Since having the conductive material, the adsorption unit 21 may be electrified as a certain polarity by the voltage applying unit 23. The adsorption unit 21 may be in the shape of a brush. The conductive material may indicate a material capable of being electrified as a certain voltage by a voltage applied by the voltage applying unit 23. The adsorption unit 21 may include an antistatic material capable of preventing an occurrence of static electricity.

The driving unit 22 transfers the adsorption unit 21 in contact with the surface of the light window 17 to allow the adsorption unit 21 formed in the shape of a brush to wipe the surface of the light window 17. The driving unit 22 transfers the adsorption unit 21 in a direction crossing a light emitting direction of the detector 10, thereby removing the part of the pollutant P attached to the light window 17 by using mechanical friction.

The voltage applying unit 23 applies a voltage with certain polarity to the adsorption unit 21 having the conductive material. For example, the voltage applying unit 23 applies a first voltage having polarity opposite to that of the pollutant P, thereby electrifying the adsorption unit 21 with the polarity opposite to the pollutant P. Accordingly, electrical fundamental forces occur between the adsorption unit 21 and the pollutant P in such a way that the pollutant P are adsorbed to the adsorption unit 21.

The control unit 24 controls whether the voltage applying unit 23 applies a voltage and the polarity of the voltage and controls whether the driving unit 22 drives and a driving direction.

Figure 5:
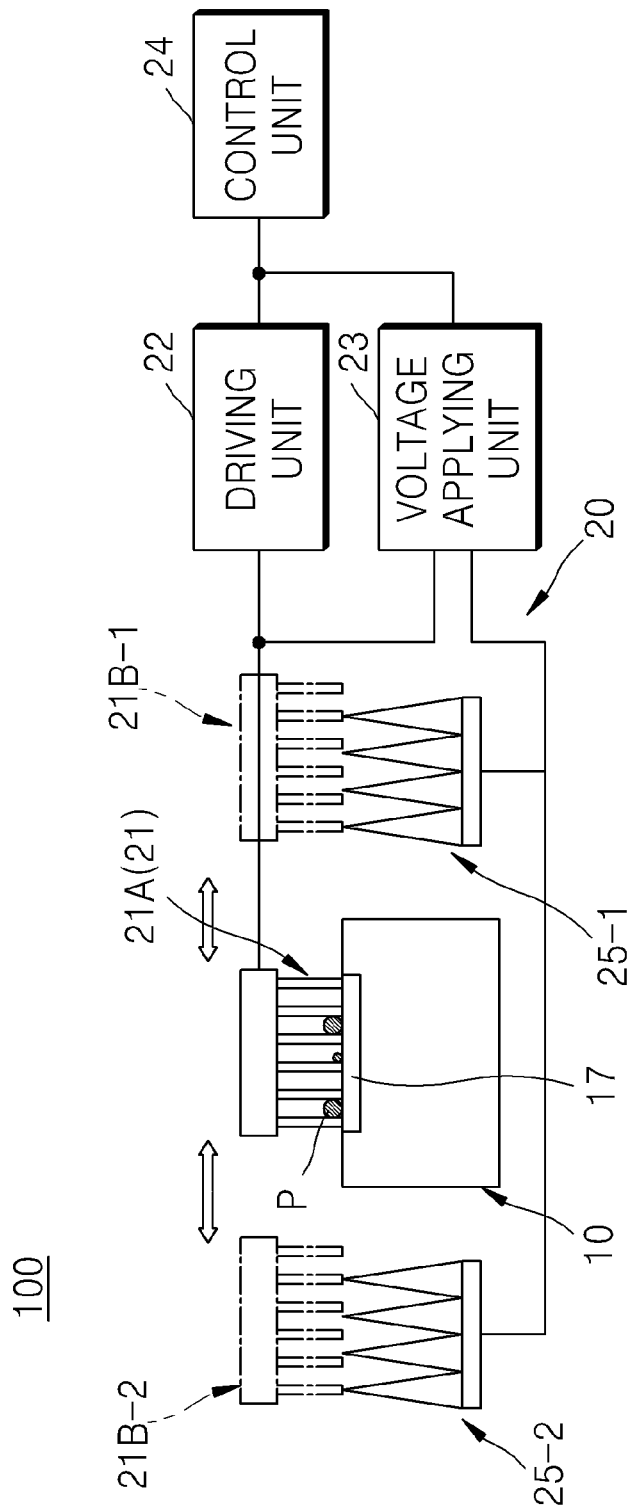
FIGS. 5 to 7 illustrate exemplary locations of an adsorption unit in a detection device.
Figure 7:
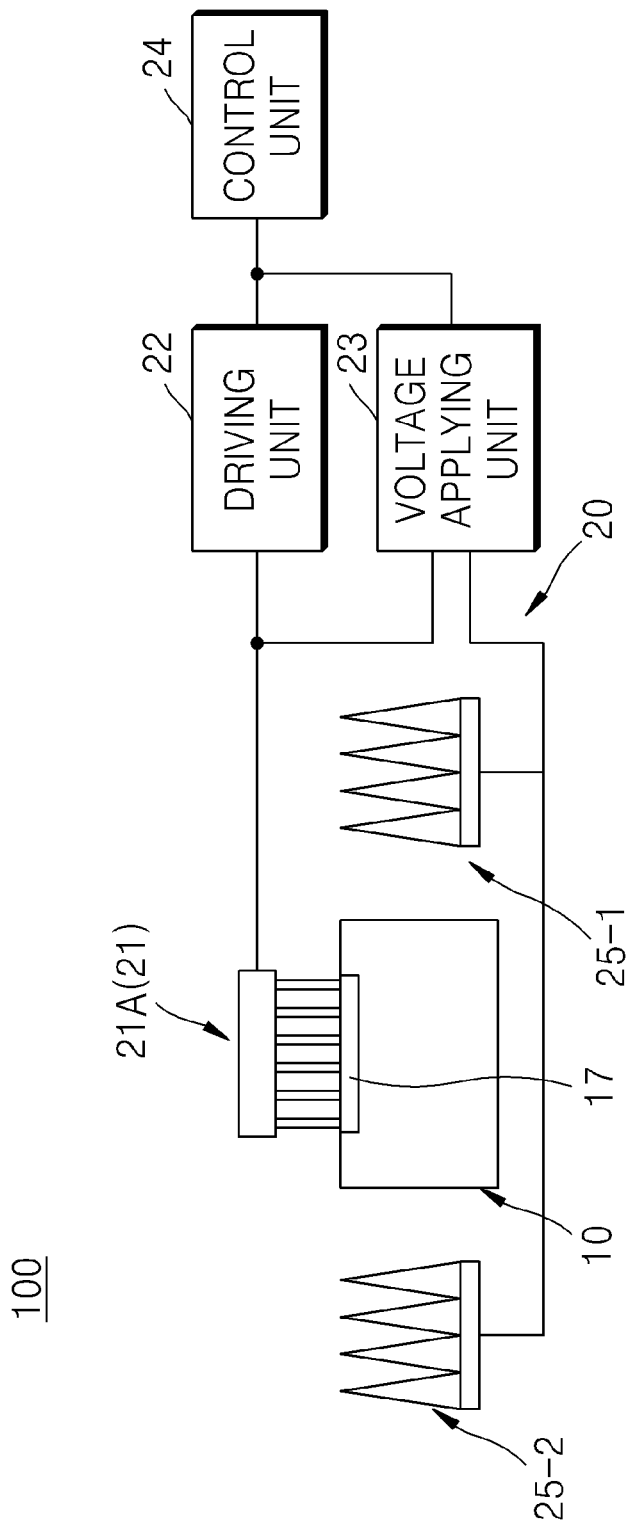

FIGS. 5 and 7 illustrate exemplary locations of the adsorption unit 21 of the detection device 100.

Referring to FIG. 5, the adsorption unit 21 may be transferred to a first location 21A for being in contact with the light window 17 and second locations 21B-1 and 21B-2 for releasing a contact with the light window 17. The exemplary second locations 21B-1 and 21B-2, as illustrated in the drawing, may include other locations when the adsorption unit 21 is transferred between to the left and right of the detector 10. The control unit 24 controls the driving unit 22 to transfer the adsorption unit 21 to one of the first location 21A and the second locations 21B-1 and 21B-2. The control unit 24 determines whether the voltage applying unit 23 applies a voltage and the polarity of the voltage according to a location of the adsorption unit 21. For example, when the adsorption unit 21 is located in the first location 21A, the control unit 24 controls the voltage applying unit 23 to apply the first voltage to the adsorption unit 21 to adsorb the pollutant P. The first voltage, for example, may be a voltage with a polarity opposite to that of the pollutant P. Through this, a part of the pollutant P attached to the light window 17 may be removed by the mechanical friction with the adsorption unit 21 and a part thereof may be adsorbed onto the adsorption unit 21 due to the electrical fundamental forces of the adsorption unit 21.

Figure 6:
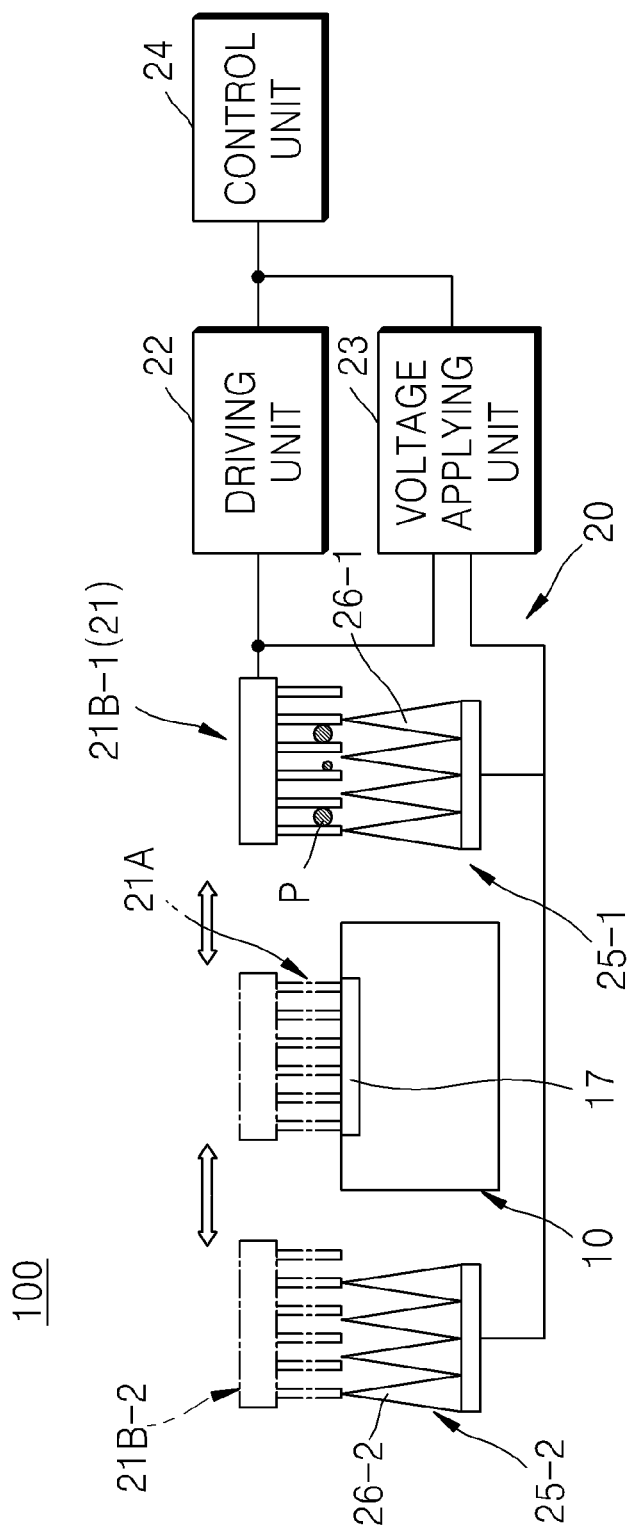

Referring to FIG. 6, when the adsorption unit 21 is located at one of the second locations 21B-1 and 21B-2, the control unit 24 may control a separation of the pollutant P adsorbed onto the adsorption unit 21. While the pollutant P adsorbed onto the adsorption unit 21 is not being eliminated or separated from the adsorption unit 21, when the adsorption unit 21 is transferred to the first location 21A, not only an adsorption efficiency may decrease but also the pollutant P adsorbed onto the adsorption unit 21 may contaminate more of the light window 17. However, in accordance with an exemplary embodiment of the present invention, the pollutant P adsorbed onto the adsorption unit 21 is eliminated in one of the second locations 21B-1 and 21B-2 for releasing a contact with the light window 17, thereby protecting the adsorption unit 21 from being contaminated by the pollutant P and allowing the adsorption unit 21 to be repetitively used.

The pollutant P adsorbed onto the adsorption unit 21 may be collected by pollutant collecting units 25-1 and 25-2. The pollutant collecting units 25-1 and 25-2 may be arranged separately from the detector 10. The pollutant collecting units 25-1 and 25-2 may include contact projections 26-1 and 26-2 projected in a direction crossing a transfer path of the adsorption unit 21. For example, the adsorption unit 21 is in contact with contact projections 26-1 and 26-2 while being transferred from the first location 2A to one of the second locations 21B-1 and 21B-2 or from one of the second locations 21B-1 and 21B-2 to the first location 2A. Due to mechanical friction between the adsorption unit 21 and the contact projections 26-1 and 26-2 of the pollutant collecting units 25-1 and 25-2, a part of the pollutant P adsorbed onto the adsorption unit 21 may be dropped onto the pollutant collecting units 25-1 and 25-2.

A residual pollutant P may not be separated from the adsorption unit 21 despite the mechanical friction with the contact projections 26-1 and 26-2 due to electrical fundamental forces or repulsive forces. The voltage applying unit 23 may apply a second voltage for separating the pollutant P from the adsorption unit 21 to the adsorption unit 21 when the adsorption unit 21 is located in one of the second locations 21B-1 and 21B-2. The voltage applying unit 23 may apply a third voltage for collecting the pollutant P attached to the adsorption unit 21 into the pollutant collecting units 25-1 and 25-2 to the pollutant collecting units 25-1 and 25-2. As an example, the voltage applying unit 23 may apply a voltage with the same polarity as that of the pollutant P to the adsorption unit 21 located in one of the second locations 21B-1 and 21-2, thereby generating electrical repulsive forces between the adsorption unit 21 and the pollutant P adsorbed onto the adsorption unit 21. Due to such electrical repulsive forces, the pollutant P may be separated from the adsorption unit 21 and may be collected into the pollutant collecting units 25-1 and 25-2. To allow the pollutant P to be efficiently collected into the pollutant collecting units 25-1 and 25-2, the voltage applying unit 23 may apply a voltage with polarity opposite to the pollutant P to the pollutant collecting units 25-1 and 25-2. Via this, electrical repulsive forces act between the adsorption unit 21 and the pollutant P, thereby collecting the pollutant P separated from the adsorption unit 21 into the pollutant collecting units 25-1 and 25-2. As an example, the voltage applying unit 23 may apply a ground voltage, that is, 0 V to the adsorption unit 21 and apply a voltage with polarity opposite to the pollutant P to the pollutant collecting units 25-1 and 25-2. Via this, the electrical repulsive forces between the adsorption unit 21 and the pollutant P are released and electrical repulsive forces are generated between the pollutant collecting units 25-1 and 25-2. Due to the electrical repulsive forces acting between the pollutant collecting units 25-1 and 25-2 and the pollutant P, the pollutant P may be separated from the adsorption unit 21 and collected into the pollutant collecting units 25-1 and 25-2. A voltage level of the voltage applying unit 23 and whether to apply a voltage may be controlled by the control unit 24.

Toner forming the toner image I on the intermediate transfer belt 127 has one polarity such as negative, but the pollutants P such as toner scattered while forming the toner image I may have a positive polarity in addition to the negative polarity due to other environmental factors. When the pollutants P have both negative and positive polarities, adsorbing the pollutants P by the adsorption unit 21 may be performed several times. For example, the voltage applying unit 23 may periodically convert and apply a voltage with positive or negative polarity opposite to that of the pollutant P.

As an example, to allow the adsorption unit 21 to adsorb the pollutant P with negative polarity, the voltage applying unit 23 applies a voltage with positive polarity to the adsorption unit 21 located in the first location 21A. When adsorbing the pollutant P with negative polarity by the adsorption unit 21 is finished, the adsorption unit 21 is transferred to the 2-1 location 21B-1 and a voltage with negative polarity is applied to the adsorption unit 21 in such a way that the pollutant P with negative polarity adsorbed onto the adsorption unit 21 are dropped onto the pollutant collecting unit 25-1. The adsorption unit 21 from which the pollutant P with negative polarity are separated and removed is transferred to the first location 21A. To allow the adsorption unit 21 to adsorb the pollutant P with positive polarity, the voltage applying unit 23 applies a voltage with negative polarity to the adsorption unit 21. When adsorbing the pollutant P with positive polarity by the adsorption unit 21 is finished, the adsorption unit 21 is transferred to the 2-2 location 21B-2 and a voltage with positive polarity is applied to the adsorption unit 21 in such a way that the pollutant P with positive polarity adsorbed onto the adsorption unit 21 are dropped onto the pollutant collecting unit 25-2. In other words, to allow the adsorption unit 21 to adsorb and remove the pollutant with positive and negative polarities attached to the light window 17, the voltage applying unit 23 converts the polarity of a voltage applied to the adsorption unit 21, depending on the location of the adsorption unit 21 and whether the pollutant P are adsorbed onto the adsorption unit 21.

Figure 8:
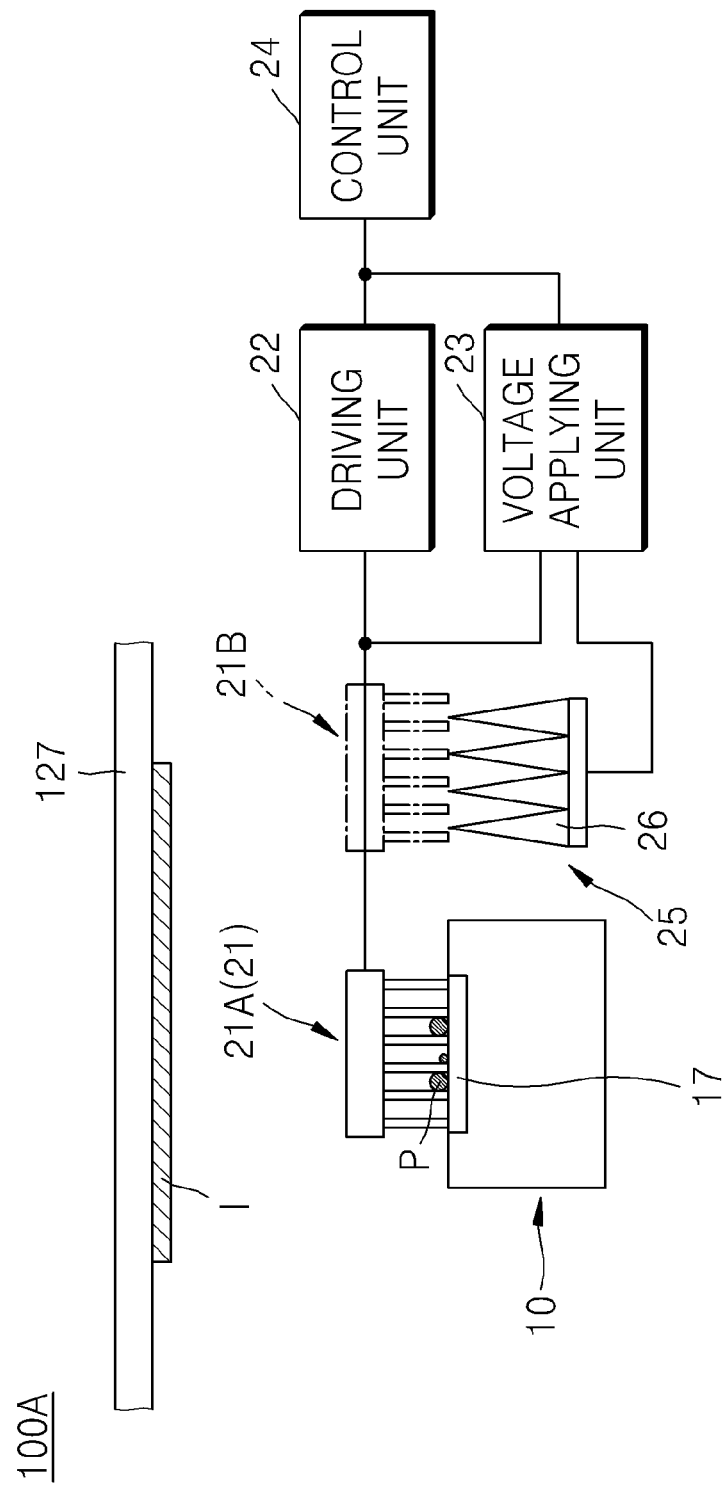
FIG. 8 illustrates an exemplary detection device according to an embodiment of the present invention.

According to an exemplary embodiment, when the pollutant P have a plurality of polarities, the adsorption unit 21 reciprocates between the two pollutant collecting units 25-1 and 25-2 arranged interposing the detector 10 therebetween. However, it is not limited thereto and the adsorption unit 21 may reciprocate between the detector 10 and a single collecting unit 25 located on one side of the detector 10 and may remove the pollutant P with a plurality of polarities, as illustrated in FIG. 8. When the pollutants P substantially have one polarity, for example, a negative polarity, the adsorption unit 21 may reciprocate between the detector 10 and the single collecting unit 25 located on one side of the detector 10 and may remove the pollutant P with negative polarity.

Referring to FIG. 7, after the pollutant P adsorbed onto the adsorption unit 21 is dropped onto the second locations 21B-1 and 21B-2 as illustrated in FIG. 6, that is, separating the pollutant P from the adsorption unit 21 is finished, the voltage applying unit 23 may apply a fourth voltage to the adsorption unit 21 to prevent the pollutant P being attached to the light window 17. The voltage applying unit 23 may electrify the light window 17 via the adsorption unit 21. The pollutant P attached to the surface of the light window 17 is removed while adsorption and separation processes of the adsorption unit 21 are being performed as illustrated in FIGS. 5 and 6. However, as illustrated in FIG. 5, while adsorbing the pollutant P, due to friction with the adsorption unit 21 to which a voltage with polarity opposite to that of the pollutant P is applied, the surface of the light window 17 may be inadvertently electrified with a polarity opposite to that of the pollutant P. Due to this, the surface of the light window 17 may be in a state in which the pollutant P are attached thereto. Accordingly, the voltage applying unit 23 may electrify the surface of the light window 17 by applying the fourth voltage to the adsorption unit 21 to prevent attachment of the pollutant P to the surface of the light window 17. As an example, the light window 17 may be electrified as a ground state. For this, the voltage applying unit 23 may apply a ground voltage to the adsorption unit 21. When the light window 17 is electrified as the ground state, the pollutant P being attached to the light window 17 may be prevented though the pollutant P have both positive and negative polarities. As an example, the light window 17 may be electrified as the same polarity as the pollutant P. The voltage applying unit 23 may apply a voltage with the same polarity as the pollutant P to the adsorption unit 21. When the pollutant P substantially have one polarity such as negative polarity, the surface of the light window 17 is electrified as the negative polarity same as the pollutant P, thereby preventing the pollutant P being attached to the surface of the light window 17 due to electrical repulsive forces.

Figure 9:
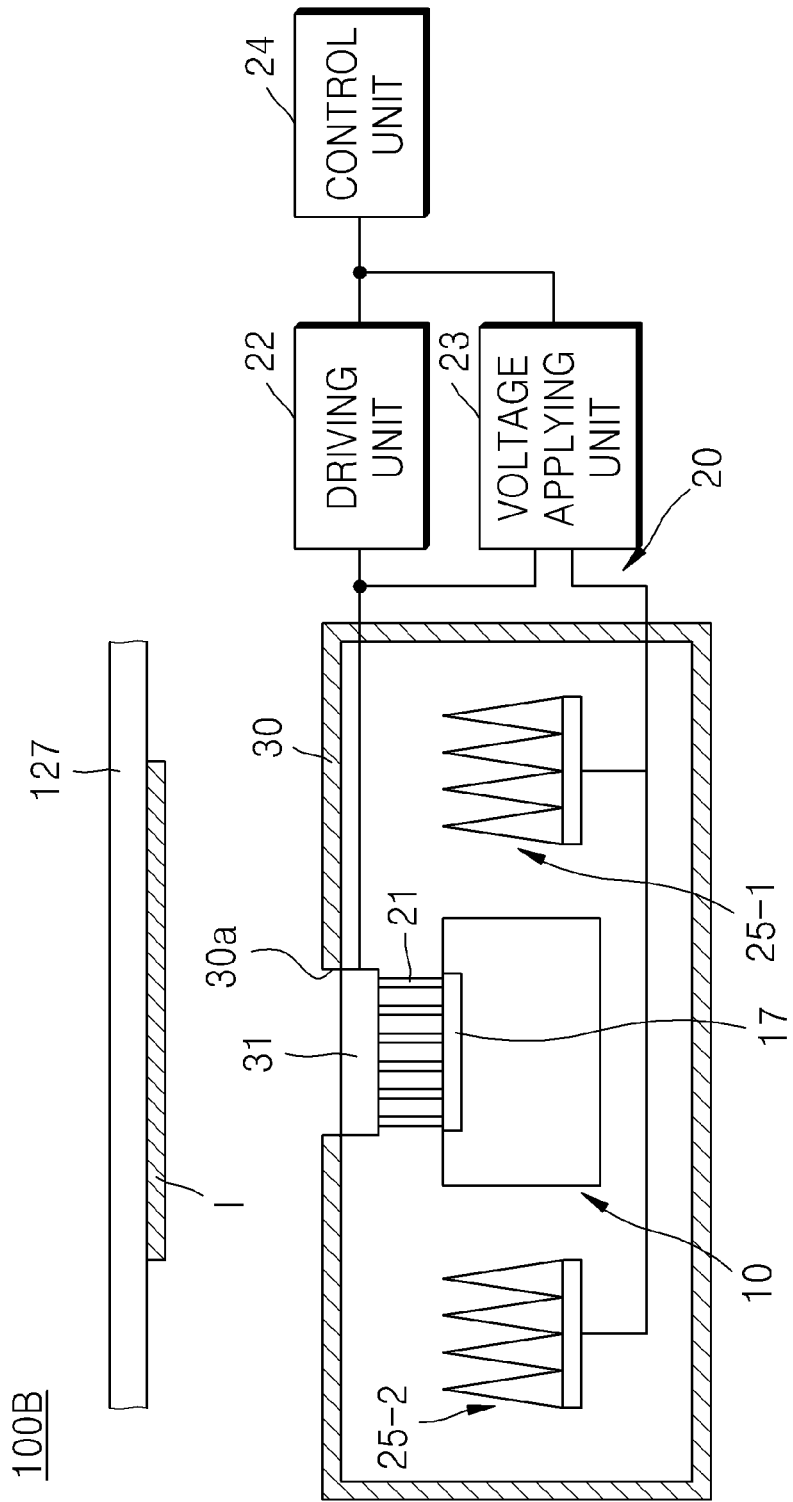
FIG. 9 illustrates a detection device according to an embodiment of the present invention.

FIG. 9 illustrates a detection device 1008 according to an embodiment of the present invention. Referring to FIG. 9, the detection device 100B may include the detector 10, the cleaner 20, a housing 30, and a shutter 31.

The housing 30 may contain the detector 10 and be installed in the image forming apparatus. The housing 30 may include an opening 30a between the light window 17 and the intermediate transfer belt 127 that is an image bearing member, to allow light to pass through.

The shutter 31 is for determining an exposure of the detector 10 and may open or close the opening 30a. The shutter 31 protects the detector 10 from being exposed to and contaminated by the pollutant P such as toner by closing the opening 30a when the detector 10 does not operate. The shutter 31 allows light to pass through between the light window 17 and the intermediate transfer belt 127 by opening the opening 30a when the detector 10 operates.

The adsorption unit 21 may be installed on the shutter 31. For example, the adsorption unit 21 may be installed on a surface of the shutter 31 facing the detector 10. As the shutter 31 is transferred, the adsorption unit 21 installed on the shutter 31 may remove the pollutant P attached to the light window 17. In other words, when the shutter 31 closes the opening 30a, the adsorption unit 21 is in contact with a top of the light window 17 and adsorbs the pollutant P. When the shutter 31 opens the opening 30a, the adsorption unit 21 is separated from the light window 17 and the pollutant P adsorbed onto the adsorption unit 21 may be dropped.

FIGS. 10A to 10E illustrate exemplary operations of a detecting device, e.g., the detecting device 100 of FIG. 2. FIG. 11 is an exemplary a timing chart illustrating a direction of controlling the driving unit 22, a sequence of turning on/off the driving unit 22, and a voltage applying state of the voltage applying unit 23 according to the sequence of FIGS. 10A to 10E.

Figure 10A:
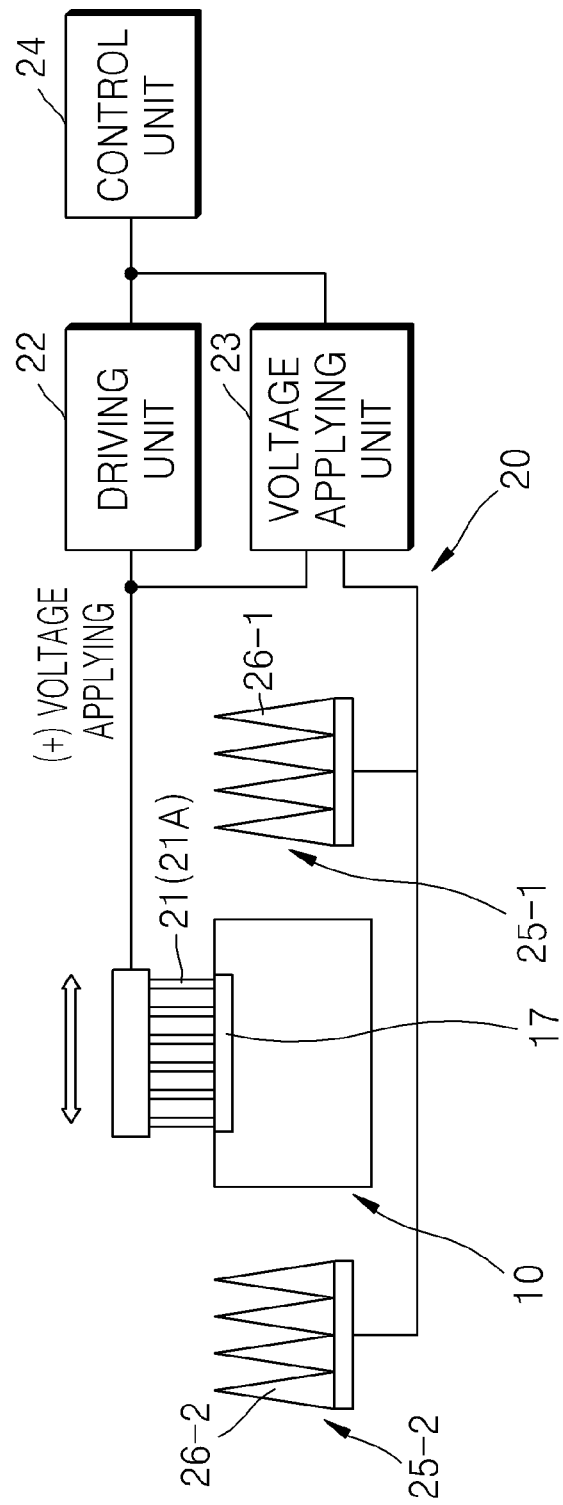
FIGS. 10A to 10E illustrate an exemplary operation state of the detection device.
Figure 11:
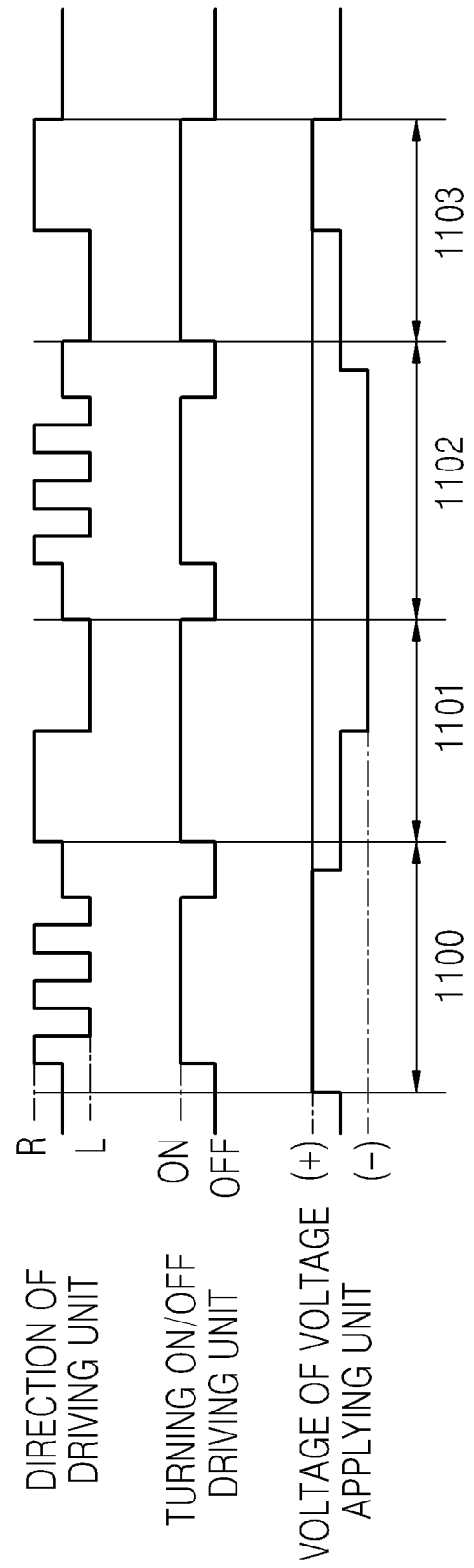
FIG. 11 is a timing chart illustrating an exemplary direction of controlling a driving unit, a sequence of turning on/off the driving unit, and a voltage applying state of a voltage applying unit according to the exemplary sequence of FIGS. 10A to 10E.

Referring to FIG. 10A and section 1100 in FIG. 11, the voltage applying unit 23 applies a positive voltage to the adsorption unit 21 and the driving unit 22 controls the adsorption unit 21 to reciprocate left and right while being in contact with the light window 17. Due to the reciprocation of the adsorption unit 21, friction is applied to the pollutant P attached to the light window 17, and as a result thereof, the pollutant P attached to the light window 17 is separated from the light window 17. A pollutant P with negative polarity separated from the light window 17 due to the reciprocation of the adsorption unit 21 and a pollutant P with negative polarity attached to the light window 17 are adsorbed onto the adsorption unit 21 due to electrical fundamental forces with the adsorption unit 21 with positive polarity.

Figure 10B:
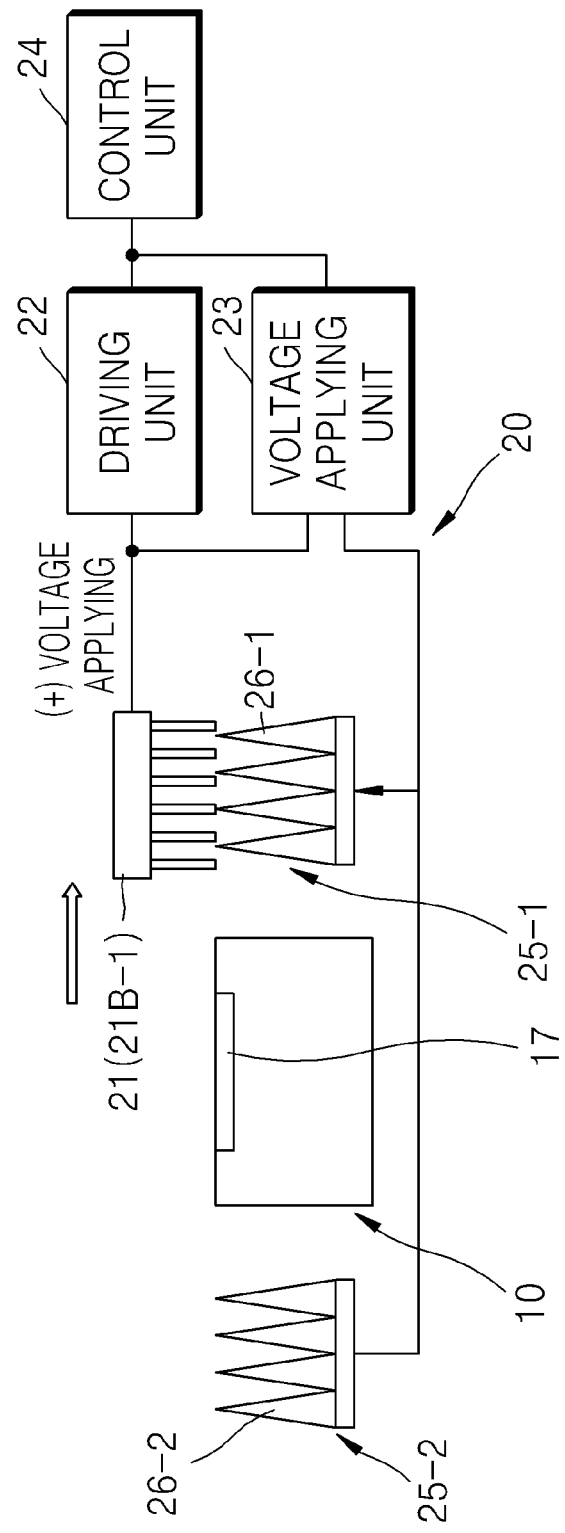
Figure 10C:
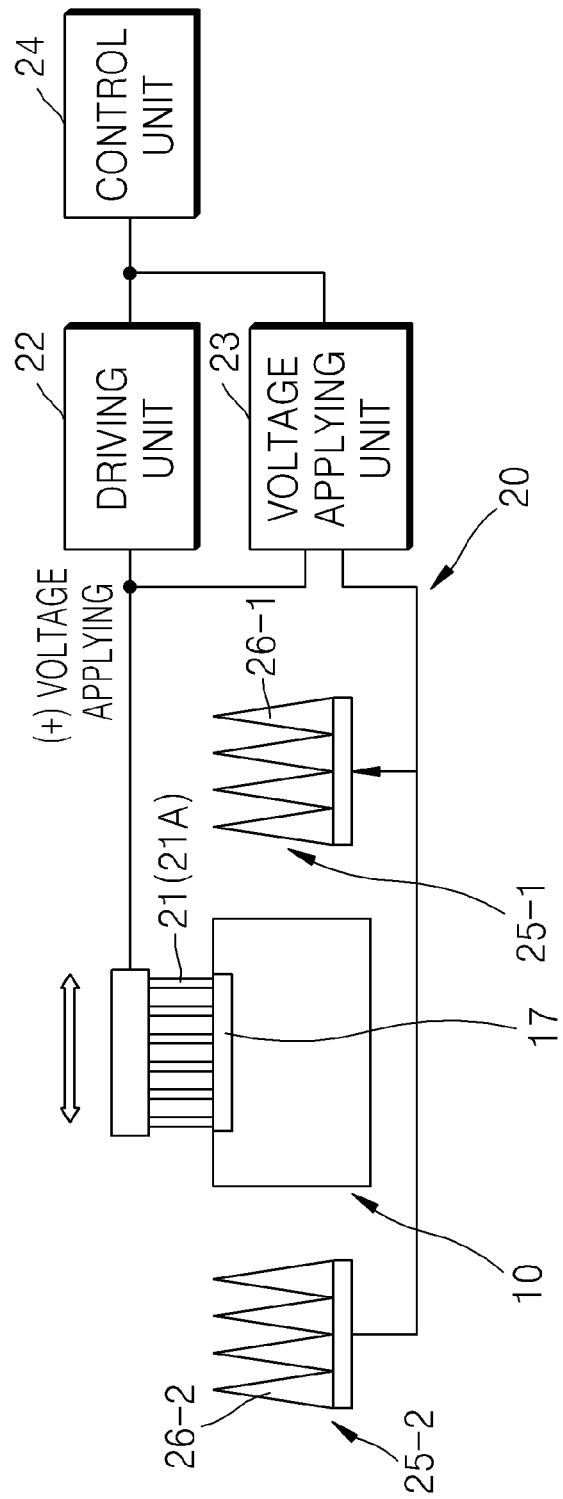

Referring to FIGS. 10B and 1101 in FIG. 11, the adsorption unit 21 adsorbing the pollutant P with negative polarity is transferred to the right side of the detector 10 and arrives at the first pollutant collecting unit 25-1 located on the right side of the detector 10. While arriving at the first pollutant collecting unit 25-1, the adsorption unit 21 is in contact with the contact projection 26-1 of the first pollutant collecting unit 25-1 and a part of the pollutant P adsorbed onto the adsorption unit 21 is preliminary dropped due to friction between the adsorption unit 21 and the contact projection 26-1. While the adsorption unit 21 is transferred left toward the detector 10, the adsorption unit 21 is in contact with the contact projection 26-1 of the first pollutant collecting unit 25-1 and a part of the pollutant P adsorbed onto the adsorption unit 21 is secondarily dropped due to friction between the adsorption unit 21 and the contact projection 26-1. A residual part of the pollutant P, despite the friction with the contact projection 26-1, may be dropped onto the first pollutant collecting unit 25-1 due to electrical fundamental forces or repulsive forces. As an example, in the second locations 21B-1 and 21B-2, where the adsorption unit 21 arrives at the first pollutant collecting unit 25-1 as the section b illustrated in FIG. 11, a negative voltage opposite to the first location 21A may be applied to the adsorption unit 21, thereby generating electrical repulsive forces between the adsorption unit 21 and the pollutant P. Due to such electrical repulsive forces, the pollutant P with negative polarity may be separated from the adsorption unit 21. As another example, though there is not shown in the drawings, a voltage applied to the adsorption unit 21 may be blocked or a ground voltage may be applied thereto and a positive voltage is applied to the first pollutant collecting unit 25-1, thereby collecting the pollutant P into the first pollutant collecting unit 25-1 due to electrical fundamental forces generated between the pollutant P with negative polarity and the first pollutant collecting unit 25-1.

Referring to FIG. 100 and section 1102 of FIG. 11, the adsorption unit 21 is transferred to the first location 21A for being in contact with the light window 17. A negative voltage is applied to the adsorption unit 21 and the adsorption unit 21 is controlled to reciprocate left and right while being in contact with the light window 17. Due to friction with the adsorption unit 21, the pollutant P attached to the light window 17 is separated. On the other hand, the pollutant P with positive polarity not adsorbed in the process illustrated in FIG. 10A may be adsorbed onto the adsorption unit 21 to which the negative voltage is applied, due to electrical fundamental forces.

Figure 10D:
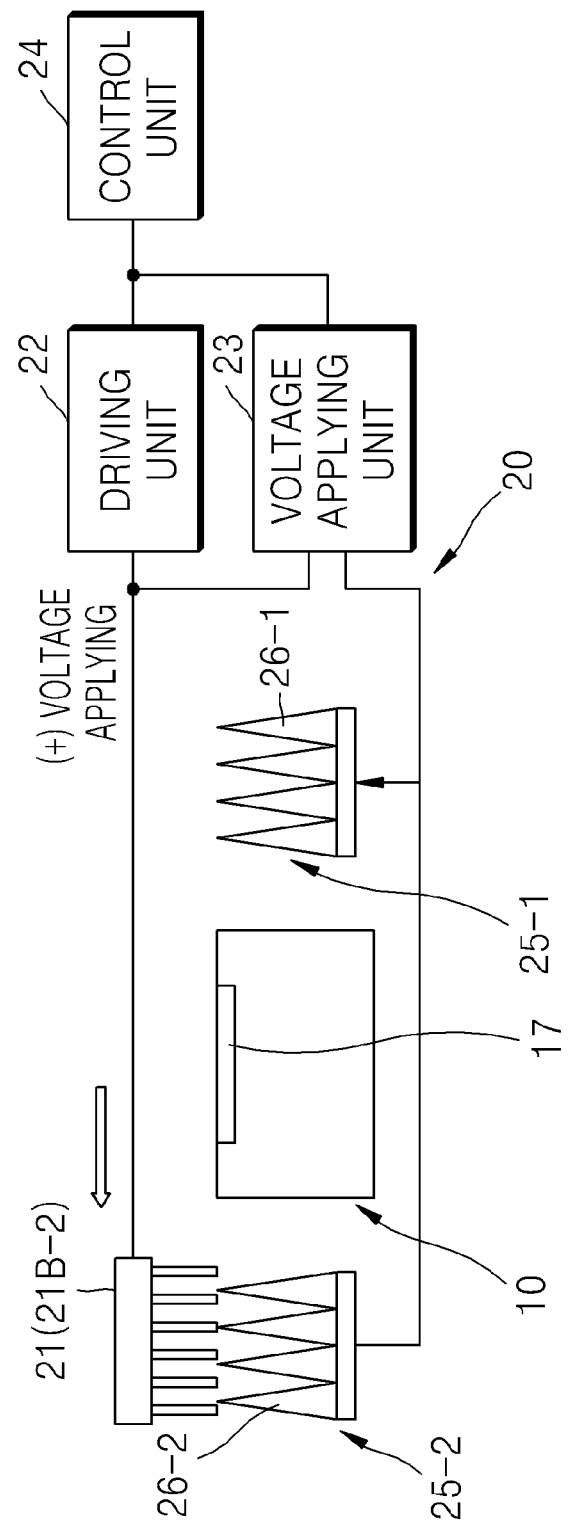

Referring to FIG. 10D and section 1103 of FIG. 11, while adsorbing the pollutant P with positive polarity, the adsorption unit 21 is transferred to the left side of the detector 10 and arrives at the second pollutant collecting unit 25-2 located on the left side of the detector 10. While arriving at the second pollutant collecting unit 25-2, the adsorption unit 21 is in contact with the contact projection 26-2 of the second pollutant collecting unit 25-2 and a part of the pollutant P adsorbed onto the adsorption unit 21 is preliminary dropped due to friction between the adsorption unit 21 and the contact projection 26-2. While the adsorption unit 21 is transferred right toward the detector 10, the adsorption unit 21 is in contact with the contact projection 26-2 of the second pollutant collecting unit 25-2 and an part of the pollutant P adsorbed onto the adsorption unit 21 is secondarily dropped due to friction between the adsorption unit 21 and the contact projection 26-2. A residual part of the pollutant P despite the friction with the contact projection 26-2 may be dropped onto the second pollutant collecting unit 25-2 due to electrical fundamental forces or repulsive forces.

Figure 10E:
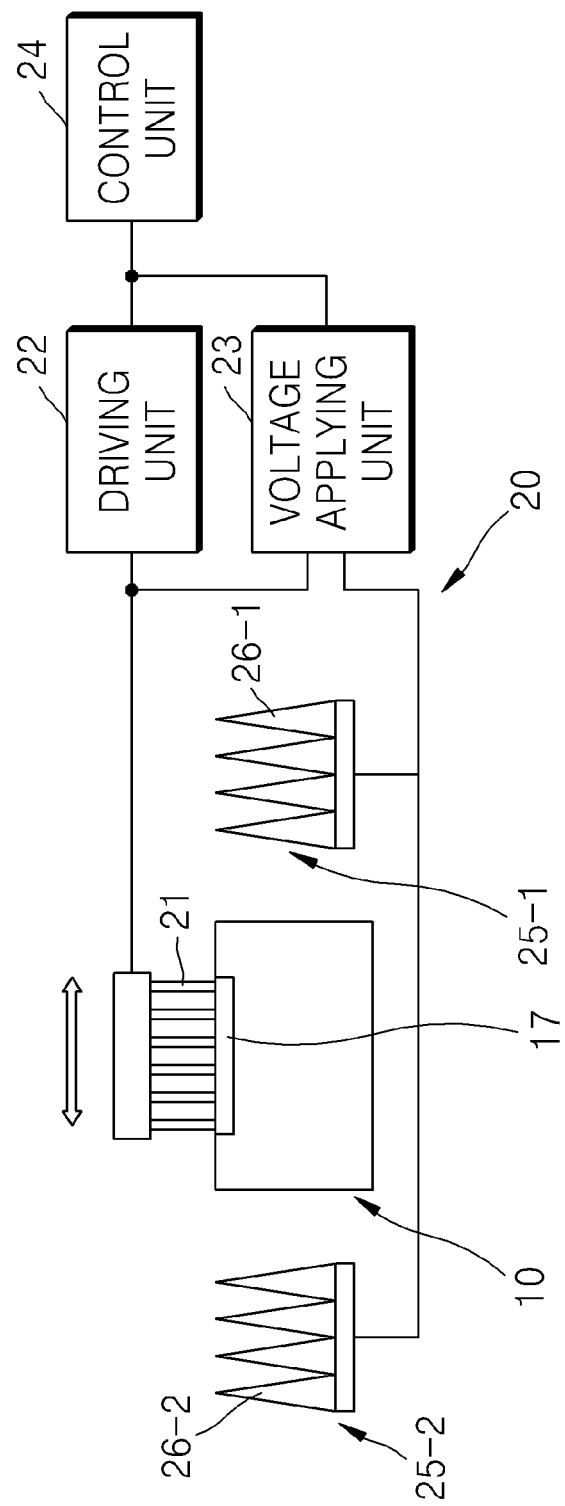

With exemplary processes illustrated in FIGS. 10A to 10D, the adsorption unit 21 has removed the pollutant P attached to the light window 17. However, the light window 17 may inadvertently have a certain polarity due to a contact with the adsorption unit 21. In this case, the light window 17 may be in a state in which the pollutant are firmly attached thereto. Accordingly, as illustrated in FIG. 10E, after the process of separating the pollutant P adsorbed onto the adsorption unit 21, the polarity of the light window 17 is removed, thereby preventing the pollutant P with a polarity being attached to the light window 17. As an example, the voltage applying unit 23 may apply a ground voltage to the adsorption unit 21. As an example, when the pollutants P substantially have one polarity, the voltage applying unit 23 may apply a voltage with the same polarity as the pollutants P to the adsorption unit 21.

On the other hand, pollutant removing operations of the detection device 100 may be performed in a certain condition. For example, when a detected calibration value of the detector 10 is changed, the cleaner 20 may be operated. Calibration may be defined an operation of adjusting a current of the light emitting portion 11 to allow the detector 10 to uniformly maintain a light-receiving value with respect to a certain reflector (not shown). Accordingly, when the calibration value is different from a certain reference value, since it can be expected that the light window 17 is contaminated, the cleaner 20 may be operated to remove the pollutant P attached to the light window 17.

As an example, when there is no printing operation for more than a certain amount of time, the cleaner 20 may be operated. Due to characteristics of toner, when the toner is left as it is and there is no printing operation for more than a certain amount of time, the polarity of the toner inside the developing unit 110 is deteriorated, thereby decreasing transfer ability of the toner with respect to the photosensitive bodies 111 to 115 or the intermediate transfer belt 127. According thereto, a large amount of toner may be scattered, which may contaminate the light window 17 of the detector 10. Accordingly, when there is no operation for more than a certain amount of time, to remove the pollutant P attached to the light window 17, the cleaner 20 may be operated.

Exemplary embodiments have been described with reference to the drawings. For example, in the described embodiments, the detector detecting concentration of the toner image has been described as the detector 10 but is not limited thereto. The detector may be optically detect a state of the toner image, for example, a detector for auto color registration detects toners with a plurality of colors are properly aligned on an image bearing member. According to an exemplary embodiment, an image forming apparatus forming a color image by using toners with colors of cyan, magenta, yellow, and black has been described but is not limited thereto. The image forming apparatus according to an exemplary embodiment may be applied to image forming apparatuses forming an image on a recording medium by using various methods such as image forming apparatuses using toner with a single color.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A detection device comprising:
 a detector having a light window capable of allowing light to pass through and detecting a state of a toner image formed on an image bearing member via the light window; and
 a cleaner removing a pollutant attached to a surface of the light window,
 wherein the cleaner comprises:
  an adsorption unit formed of a conductive material and reciprocating while being in contact with a surface of the light window, and
  a voltage applying unit applying a first voltage for adsorbing the pollutant to the adsorption unit.

2. The detection device of claim 1, further comprising:
 a housing containing the detector, the housing with an opening between the light window and the image bearing member to allow light to pass through; and
 a shutter opening and closing the opening.

3. The detection device of claim 2, wherein the adsorption unit is installed on a surface of the shutter facing the detector, and wherein the adsorption unit removes the pollutant attached to the light window by a transfer of the shutter.

4. An image forming apparatus comprising the detection device of claim 1.

5. The apparatus of claim 4, further comprising:
a housing containing the detector, the housing with an opening between the light window and the image bearing member to allow light to pass through; and
a shutter opening and closing the opening.

6. The apparatus of claim 5, wherein the adsorption unit is installed on a surface of the shutter facing the detector, and
wherein the adsorption unit removes the pollutant attached to the light window by a transfer of the shutter.

7. The detection device of claim 1, wherein the adsorption unit is capable of being transferred to a first location for being in contact with the light window and a second location for releasing a contact with the light window.

8. The detection device of claim 7, wherein the voltage applying unit applies the first voltage for adsorbing the pollutant to the adsorption unit when the adsorption unit is located in the first location.

9. The detection device of claim 8, wherein the first voltage is a voltage having a polarity opposite to the pollutant.

10. The detection device of claim 9, wherein the polarity of the first voltage is periodically converted.

11. The detection device of claim 7, wherein the cleaner further comprising a pollutant collecting unit collecting the pollutant.

12. The detection device of claim 11, wherein the pollutant collecting unit comprises a contact projection projected crossing a transfer path of the adsorption unit and being in contact with the adsorption unit.

13. The detection device of claim 11, wherein the voltage applying unit applies a second voltage for separating the pollutant from the adsorption unit to the adsorption unit when the adsorption unit is located in the second location.

14. The detection device of claim 13, wherein the second voltage is one of a voltage having the same polarity as the pollutant and a ground voltage.

15. The detection device of claim 13 wherein the voltage applying unit applies a third voltage for collecting the pollutant into the pollutant collecting unit to the pollutant collecting unit when the adsorption unit is located in the second location.

16. The detection device of claim 15, wherein the third voltage is a voltage having polarity opposite to the pollutant.

17. The detection device of claim 13, wherein the voltage applying unit applies a fourth voltage for preventing the pollutant being attached to the light window to the adsorption unit.

18. The detection device of claim 17, wherein the fourth voltage is one of a voltage having the same polarity as the pollutant and a ground voltage.

19. A method of removing a pollutant, performed by a detection device detecting a state of a toner image formed on an image bearing member, the method comprising:

applying, to adsorb a pollutant attached to a light window of a detector, a first voltage for adsorbing the pollutant to an adsorption unit reciprocating while being in contact with the light window; and
allowing the pollutant to be adsorbed onto the adsorption unit by using electrical fundamental forces generated between the adsorption unit and the pollutant.

20. The method of claim 19, further comprising determining an exposure of the detector via a transfer of a shutter arranged between the image bearing member and the detector.

21. The method of claim 20, wherein the adsorption unit is installed on a surface of the shutter facing the detector and removes the pollutant attached to the light window by using the transfer of the shutter.

22. The method of claim 19, wherein, in the allowing the pollutant to be adsorbed onto the adsorption unit, the adsorption unit is located in a location for being in contact with the light window.

23. The method of claim 22, wherein the first voltage is a voltage having a polarity opposite to the pollutant.

24. The method of claim 23, wherein the polarity of the first voltage is periodically converted.

25. The method of claim 22, further comprising, after the allowing the pollutant to be adsorbed onto the adsorption unit, separating the pollutant adsorbed onto the adsorption unit.

26. The method of claim 25, wherein, in the separating the pollutant, the adsorption unit is located in a location for releasing a contact with the light window.

27. The method of claim 26, wherein, in the separating the pollutant, the adsorption unit is transferred while being in contact with a contact projection formed on a pollutant collecting unit.

28. The method of claim 27, wherein, in the separating the pollutant, a second voltage for separating the pollutant adsorbed onto the adsorption unit is applied the adsorption unit.

29. The method of claim 28, wherein the second voltage is one of a voltage having the same polarity as the pollutant and a ground voltage.

30. The method of claim 28, wherein, in the separating the pollutant, a third voltage for collecting the pollutant into the pollutant collecting unit is applied to the pollutant collecting unit.

31. The method of claim 30, wherein the third voltage is a voltage having polarity opposite to the pollutant.

32. The method of claim 28, wherein, after the separating the pollutant, a fourth voltage for preventing the pollutant being attached to the light window is applied to the adsorption unit.

33. A method of removing a pollutant having a first polarity attached to a part of an image forming apparatus, the method comprising:
applying a same polarity to the part as the first polarity to repulse the pollutant from the part; and
applying an opposite polarity to the first polarity to a collector of the pollutant to attract the pollutant to be released from the part.

* * * * *